Figure 1:
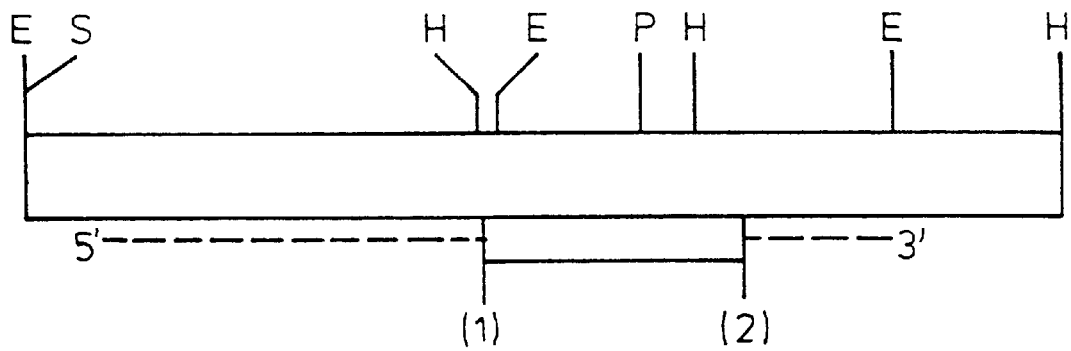

US006020129A

United States Patent
Schröder et al.

[19]

[11] Patent Number: 6,020,129

[45] Date of Patent: Feb. 1, 2000

[54] STILBENE SYNTHASE GENE

[75] Inventors: Gudrun Schröder; Joachim Schröder, both of Gundelfingen; Rüdiger Hain, Langenfeld; Peter Helmut Schreier, Cologne, all of Germany

[73] Assignee: Bayer Aktiengesellschaft, Leverkusen, Germany

[21] Appl. No.: 08/901,974

[22] Filed: Jul. 28, 1997

Related U.S. Application Data

[63] Continuation of application No. 08/461,901, Jun. 5, 1995, Pat. No. 5,689,046, which is a continuation of application No. 07/962,993, Oct. 19, 1992, which is a continuation of application No. 07/635,814, Jan. 2, 1991, abandoned, which is a continuation of application No. 07/244,760, Sep. 14, 1988, abandoned.

[30] Foreign Application Priority Data

Sep. 30, 1987 [DE] Germany ............................. 37 33 017

[51] Int. Cl.$^7$ .............................. C12Q 1/69; C07H 21/04
[52] U.S. Cl. .............................................. 435/6; 536/24.3
[58] Field of Search ........................... 435/252.3, 252.33, 435/320.1, 6; 536/23.6, 24.1, 24.3; 935/14, 19

[56] References Cited

U.S. PATENT DOCUMENTS

| | | | |
|---|---|---|---|
| 5,391,724 | 2/1995 | Kindl et al. ............................. | 536/23.2 |
| 5,500,367 | 3/1996 | Hain et al. ............................. | 435/252.3 |
| 5,589,621 | 12/1996 | Kindl et al. ............................. | 800/205 |

OTHER PUBLICATIONS

"The Purification and Properties of a Stilbene Synthase from Induces Cell Suspension",The Journal o Biological Chemistry, vol. 259, No. 11, Jun. 10, 1984 Schoppner et al.

Maniatas et al., "Molecular Cloning of Laboratory Manual", Cold Spring Harbor Laboratory, 1982.

Melchior et al., Archives of Biochemistry & Biophysics, vol. 288, pp. 252–557 (1991).

Melchior et al., FEBS vol. 268, pp. 17–20 (1990).

Hart, "Role of Phytostilbenes in Decay and Disease Resistance", Ann.Rev.Phytopathol., pp. 437–458 (1981), vol. 19.

Schroder et al., "Molecular analysis of resveratrol synthase cDNA, genomic clones and relationship with chalcone synthase", Eur.J.Biochem. 172, 161–169 (1988).

Physiological Plant Pathology (1976),9, 77–86, "The Production of Resveratrol by *Vitus vinifera* and other members of the Vitaceae as a response to infection or injury".

"Induktions–und Nachweismethoden fur Stilbene bei Vitaceen", Vitis 23, 179–194 (1984).

Gorham and Coughlan, 1989, "Inhibition of Photosynthesis by Stilbenoids", Phytochemistry, 19: 2059–2064 (1980).

*Primary Examiner*—George C. Elliott
*Assistant Examiner*—Robert Schwartzman
*Attorney, Agent, or Firm*—Sprung Kramer Schaefer & Briscoe

[57] ABSTRACT

A stilbene synthase gene. More particularly, a stilbene synthase gene in which the stilbene synthase is resveratrol synthase. Also more particularly a stilbene synthase gene which is obtained from groundnut (Arachis hypogaea). Furthermore a stilbene synthase gene, corresponding to the stilbene synthase gene which is contained in the plasmid pGS 828.1, and DNA sequences acting in essentially the same say. Still further, a stilbene synthase gene unit which comprises approximately 6,700 base pairs and exhibits 3 EcoRI, 3 HindIII and 1 PstI cleavage sites, and which can be obtained by partial cleavage of the plasmid PGS 828.1 using EcoRI and HindIII, or from plasmid pGS 828.1 using SstI and PvuII.

1 Claim, 1 Drawing Sheet

STILBENE SYNTHASE GENE

This is a continuation, of application Ser. No. 08/461,901, filed on Jun. 5, 1995, now U.S. Pat. No. 5,629,046, which is a continuation of application Ser. No. 07/962,993, filed on Oct. 19, 1992, now pending, which is a continuation of application Ser. No. 07/635,814, filed on Jan. 2, 1991, now abandoned, which is a continuation of application Ser. No. 07/244,760, filed on Sep. 14, 1988, now abandoned.

The present invention relates to the gene, isolated from plants, for stilbene synthase and to the use of the gene for the transformation of vectors, host organisms and plants, and for the production of plants which have an increased resistance to pests.

The term stilbene describes a group of chemical substances which occur in plants and contain the stilbene skeleton (trans-1,2-diphenylethylene) as their common basic structure. This basic skeleton may be supplemented by the addition of other groups. Two important stilbenes are the 3,5-dihydroxystilbene (pinosylvine) and the 3,3',5-trihydroxystilbene (resveratrol).

Stilbenes have been found in certain trees (angiosperms, gymnosperms), but also in some herbaceous plants (in species of the Myrtaceae, Vitaceae and Leguminosae families). Stilbenes are toxic to pests, especially to fungi, bacteria and insects, and are suitable for repelling these pests. It is this ability which is also regarded as being the most important biologically. Especially in herbaceous plants, the situation is often such that stilbenes are present in only very Low concentrations in healthy tissue, but very high amounts of stilbenes are synthesized at the point of infection following infection or wounding. This increased concentration correlates with an increased pest resistance of those plants which are able to synthesize stilbenes. The ability to synthesize these substances is regarded as an important defence mechanism. Unfortunately, only a few useful plants have the ability to synthesize stilbenes, or to produce them in an amount which confers on them sufficient resistance to pests.

The key for the formation of all stilbenes is the synthesis of the basic skeleton. So far, essentially two types of enzymes have been described (resveratrol synthase and pinosylvine synthase), both of which are designated as stilbene synthases since both of them synthesize the stilbene basic skeleton. To date, the groundnut (Arachis hypogaea) resveratrol synthase has been characterized in most detail; most of the properties of this enzyme are known (Schöppner and Kindl, 1984). Both pinosylvine and resveratrol, the most simple stilbenes, have a generally toxic action, preferably microbicidal, in particular fungistatic, against infecting pest organisms. Substrates used by stilbene synthases are malonyl-CoA and cinnamoyl-CoA or coumaroyl-CoA, that is to say substances which occur in every plant, since they are also used in the biosynthesis of other important plant constituents (for example flavonoids, flower pigments). On the topic of stilbenes and stilbene synthase the following literature may be cited: Hart, J. H. (1981) Annu. Rev. Phytopathology 19, 437–458; Hart, J. H., Shrimpton, D. M. (1979) Phytopathology 69, 1138–1143; Kindl, H. (1985) in: Biosynthesis and Biodegradation of Wood Components, Ed. Higuchi, T., Academic Press, Inc., pp. 349–377 and Schöppner, A.; Kindl, H. (1984) J. Biol. Chem. 259, 6806–6811.

A large proportion of the world's yield of crop plants is continually being destroyed by pests (in 1967, the loss of potential yield was 35%; cf. Chemistry of Pesticides, edited by K. H. Buchel, John Wiley & Sons, New York, 1983, page 6). Hence there is an urgent need to research into and to exploit all possibilities which are suitable for reducing or preventing the attack of crop plants by pests.

The new gene for stilbene synthase ("stilbene synthase gene"), which can be introduced into the genotype (the genome) of plants not producing, or only insufficiently producing, stilbenes, which can result in an increased resistance of these plants to pests, has now been isolated.

By stilbene synthase gene is to be understood every nucleic acid (DNA) which, after its transcription into RNA and translation into protein (in a suitable environment) results in the production of an enzyme having the properties of a stilbene synthase (enzymatic synthesis of stilbene in a suitable environment), this nucleic acid being isolated from its natural environment, or integrated in a vector, or contained as "foreign" DNA or as "additional" DNA in a prokaryotic or eukaryotic DNA.

If the stilbene synthase gene, at its beginning and/or end, still contains DNA sequences which do not, or not considerably, impede the function of the gene, the term "gene unit" is also used hereinafter. These gene units are formed, for example, by cleavage using restriction enzymes (for example, partial cleavage with EcoRI and HindIII), due to there being no cleavage sites for customary restriction enzymes exactly at the beginning and at the end of the gene.

The stilbene synthase gene (or the gene unit) can be present in the same form as is contained in the plants, genome ("genomic" form, including sequences which do not code for stilbene synthase and/or do not have regulatory activity (such as introns), or in a form which corresponds to the cDNA (copy DNA), which can be obtained from mRNA with the aid of reverse transcriptase/polymerase (and no longer contains introns).

In the stilbene synthase gene (or the gene unit) according to the invention, DNA sections may be replaced by other DNA sections which act in essentially the same way. Also, it may, at the ends, carry those DNA sequences which are in each case adapted for the manipulation of the gene (or the gene unit) (for example "linkers").

In the present context, by "foreign" DNA there is to be understood DNA which does not occur naturally in the particular prokaryotic or eukaryotic genome, but which is introduced into this genome only by human intervention. "Additional" DNA is meant to be DNA which occurs naturally in the relevant prokaryotic or eukaryotic genome, but which is introduced into this genome in additional amounts by human intervention. According to the needs and the nature of the particular case, the "foreign" DNA or "additional" DNA may be introduced in one or several copies.

By stilbene synthase, which is synthesized with the aid of the stilbene synthase gene (or the gene unit) according to the invention in plants or plant cells, is meant every enzyme which brings about the synthesis of those plant substances defending against pests (phytoalexines) and containing the stilbene skeleton.

Preferred stilbenes are pinosylvine (3,5-dihydroxystilbene), pterostilbene (3,5-dimethoxy-4'-hydroxystilbene) and resveratrol (3,3',5-trihydroxystilbene), pinosylvine and resveratrol being particularly preferred, and resveratrol being very particularly preferred.

As already mentioned, stilbenes are found in certain tree species and also in several other, preferably dicotyledon plants. The preferred stilbene synthase gene according to the invention is the stilbene synthase gene which can be isolated from gymnosperms, especially Pinus, from angiosperms, especially dicotyledon plants, especially from groundnut (Arachis hypogaea) and from vine (Vitis), and very especially from groundnut.

BRIEF DESCRIPTIONS FOR FIG. 1 AND FIG. 2:

FIG. 1 represents the nucleic acid section which is obtained from the plasmid pGS 828.1 by partial cleavage with EcoRI and HindIII which has 6,700 nucleotide pairs, and which contains the stilbene synthase gene.

(1) and (2) denote beginning (1) and end (2) of the structural gene. The regulator part of the gene is located on the left-hand section (left of (1)). The following restriction enzyme cleavage sites are indicated:

E: EcoRI
H: HindIII
P: PstI
S: SstI

Figure 2:
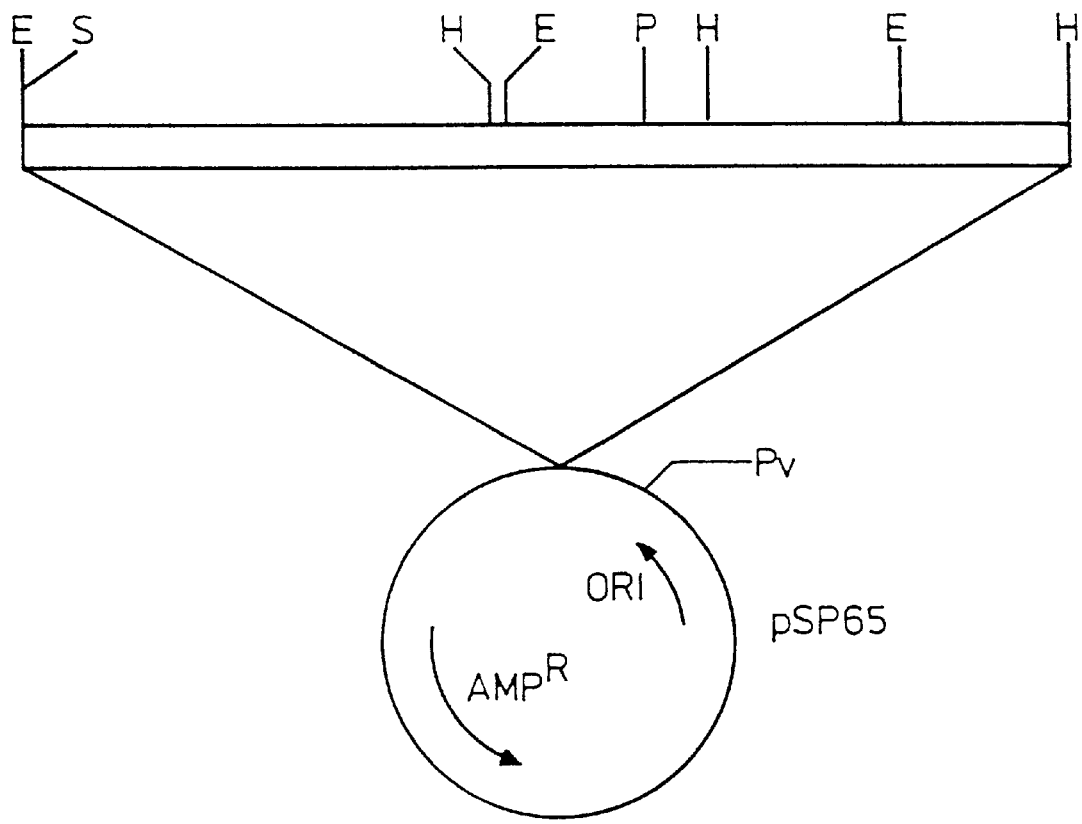

FIG. 2 represents the gene unit according to FIG. 1 in the vector pSP 65. The complete plasmid has the name pGS828.1.

"ORI" denotes origin of replication (the sequences in vector pSP65 which are important for the multiplication of the plasmid in *Escherichia coli*). "AMP$^R$" stands for the gene which brings about the resistance of pSP65-containing *Escherichia coli* to ampicillin. In addition to the cleavage sites indicated in FIG. 1, the PvuII cleavage site (which is designated as Pv) is also indicated.

The particularly preferred stilbene synthase gene according to the invention is the stilbene synthase gene which is present as a gene unit in plasmid pGS 828.1 (described in more detail below), and also the DNA sequences acting in essentially the same way.

The stilbene synthase gene comprises the 5'- and 3'-untranslated regions and an encoding region, and is located on a DNA fragment of (approx.) 6.7 kbp (gene unit). The gene unit exhibits (3) EcoRI, (3) HindIII and (1) PstI cleavage sites. It can be obtained by partial cleavage with EcoRI and HindIII from plasmid pGS 828.1.

The 5'-regulatory part is situated next to the first 7 codons of the protein-encoding region on an approx. 3.3 kbp size EcoRI fragment and preceeds the rest of the encoding region. This region comprises 1540 bp and contains an intron of 369 bp and a HindIII cleavage site. The 3'-untranslated region downstream is completely present and is limited by an EcoRI cleavage site (see FIG. 1). The gene unit which is cloned in vector pSP 65 (plasmid pGS 828.1) contains two internal EcoRI, one PstI and two HindIII cleavage sites and is limited by the SstI cleavage site (immediately next to the EcoRI cleavage site in the direction of the stilbene synthase gene) in the polylinker of the pSP 65 plasmid at the 5'-end and by the HindIII cleavage site at the 3'-end. It is particularly advantageous to obtain the gene unit with the aid of SstI and PvuII from PGS 828.1 (FIG. 2) because both cleavage sites occur only once each. The PvuII cleavage site is located outside the actual gene unit. However, this does not exert an influence on the expression of the gene in transgenic plants, and the section up to the HindIII cleavage site can be removed, if desired, using the customary methods.

*Escherichia coli* strain Nurdug 2010 containing the plasmid pGS 828.1 was deposited at the Deutsche Sammlung von Mikroorganismen (DSM), (German Collection of Microorganisms), Mascheroder Weg 1b, D-3300 Braunschweig, Federal Republic of Germany, in compliance with the provisions of the Budapest Convention on international acknowledgement of deposition of microorganisms for the purposes of patent proceedings, and has the deposit number DSM 4243 (date of deposit: Sep. 17th 1987).

This strain and its mutants and variants are also part of the present invention. In a customary fashion, the plasmid pGS 828.1 deposited in this host can easily be obtained in the amounts required by multiplication of the strain.

According to the invention, the stilbene synthase gene or the gene unit containing the (proposed) stilbene synthase-encoding DNA sequence, which is mentioned below, ("DNA sequence (protein-encoding region and intronj of the stilbene synthase gene unit from pGS 828.1"), with or without the intron or sequences acting in essentially the same way of these DNA sequences, is particularly preferred. This sequence is also part of the present invention.

Moreover, every DNA which is produced artificially, i.e., essentially non-biologically, and which contains all or part of this DNA sequence (with or without the intron) or which contains DNA sequences having essentially the same type of action, is part of the present invention.

By sequences acting in essentially the same way is meant DNA or DNA sequences which are replaced by other DNA or DNA sequences at one or several points, without, however, changing the result essentially.

Functionally complete genes, such as the stilbene synthase gene according to the invention, consist of a part with regulatory activity (especially promoter) and the structural gene, which encodes the protein stilbene synthase.

Both parts of the gene can be used independently of one another. For example, it is possible to arrange downstream of the part with regulatory activity a different DNA sequence (differing from the stilbene synthase gene), which is to be expressed after introduction in the plant's genome. Since only a few isolated promoters which are capable of displaying their action in plants or plant cells are known, the promotor of the stilbene synthase gene which is a constituent of the present invention is a valuable aid for the production of transformed plants or plant cells. It can be isolated with the aid of the SstI and EcoRI cleavage sites at the beginning of the encoding region and inserted upstream of another gene by customary methods.

It is also possible to arrange a "foreign" part with regulatory activity upstream of the stilbene synthase structural gene. This could be advantageous if in certain plants only certain (for example plant-specific) genes with regulatory activity can be sufficiently effective. The stilbene synthase structural gene (preferably the stilbene synthase-encoding DNA sequence, with or without the intron sequences and with or without their sequences acting in essentially the same way, mentioned below) therefore represents a valuable unit which can be employed on its own, and is, as has already been mentioned, also part of the present invention. The stilbene synthase gene according to the invention can be separated into the part with regulatory activity and the structural gene by customary methods. Preferably, the complete stilbene synthase gene, or the gene unit, according to the invention is used.

With the aid of customary methods, it is possible for the stilbene synthase gene, or the gene unit, or its parts, to be introduced in one or more copies (for example tandem arrangement), preferably in one copy, into any prokaryotic (preferably bacterial) or eukaryotic (preferably plant) DNA as "foreign" or "additional" DNA. The DNA thus "modified", which can, for example, be used for the transformation of plants or plant cells, and which, after transformation, is contained in plants or plant cells, is a constituent of the present invention.

The stilbene synthase gene, or the gene unit, and/or its parts, and also the modified DNA, may be present as "foreign" or "additional" DNA in vectors (in particular plasmids, cosmids or phages), in transformed microorganisms (preferably bacteria, in particular Gramnegative bacteria, such as *E. coli*), and also in transformed plant cells and plants, or in their DNA. These vectors, transformed microorganisms (which may also contain these vectors), and the transformed plant cells and plants and their DNA are constituents of the present invention.

Pests which may be mentioned against which, with the aid of the stilbene synthase gene according to the invention, resistances, or increased resistances, may be brought about, are animal pests, such as insects, mites and nematodes and microbial pests, such as phytopathogenic fungi and bacteria. Microbial pests, in particular phytopathogenic fungi.

Noxious insects are in particular insects of the orders:
Orthoptera, Dermaptera, Isoptera, Thysanoptera, Heteroptera, Homoptera, Lepidoptera, Coleoptera, Hymenoptera and Diptera.

Noxious mites are in particular:
Tarsonemus spp., Panonychus spp. and Tetranychus spp.

Noxious nematodes are in particular:
Pratylenchus spp., Heterodera spp. and Meloidogyne spp.

Microbial pests are in particular the phytopathogenic fungi:
Plasmodiophoromycetes, Oomycetes, Chytridiomycetes, Zygomycetes, Ascomycetes, Basidiomycetes, Deuteromycetes.

Phytopathogenic bacteria are in particular the Pseudomonadaceae, Rhizobiaceae, Enterobacteriaceae, Corynebacteriaceae and Streptomycetaceae.

Some pathogens of fungal and bacterial diseases which are encompassed by the abovementioned generic terms and which may be mentioned as examples, but not by way of limitation, are: Xanthomonas species such as, for example, *Xanthomonas campestris* pv. oryzae;
Pseudomonas species such as, for example, *Pseudomonas syringae* pv. lachrymans;
Erwinia species such as, for example, *Erwinia amylovora*; Pythium species, such as, for example, *Pythium ultimum*; Phytophthora species such as, for example, *Phytophthora infestans*;
Pseudoperonospora species such as, for example, *Pseudoperonospora humuli* or *Pseudoperonospora cubense*;
Plasmopara species such as, for example, *Plasmopara viticola*;
Peronospora species such as, for example, *Peronospora pisi* or *P. brassicae*;
Erysiphe species, such as, for example, *Erysiphe graminis*; Sphaerotheca species such as, for example, *Sphaerotheca fuliginea*;
Podosphaera species such as, for example, *Podosphaera leucotricha*;
Venturia species such as, for example, *Venturia inaequalis*; Pyrenophora species such as, for example, *Pyrenophora teres* or *P. graminea* (conidia form: *Drechslera, syn*: Helminthosporium);
Cochliobolus species such as, for example, *Cochliobolus sativus* (conidia form: *Drechslera, syn*: Helminthosporium);
Uromyces species such as, for example, *Uromyces appendiculatus*;
Puccinia species such as, for example, *Puccinia recondita*; Tilletia species such as, for example, *Tilletia caries*;
Ustilago species such as, for example, *Ustilago nuda* or *Ustilago avenae*;
Pellicularia species such as, for example, *Pellicularia sasakii*;
Pyricularia species such as, for example, *Pyricularia oryzae*; Fusarium species such as, for example, *Fusarium colmorum*;
Botrytis species such as, for example, *Botrytis cinerea*; Septoria species such as, for example, *Septoria nodorum*; Leptosphaeria species such as, for example, *Leptosphaeria nodorum*;
Cercospora species such as, for example, *Cercospora canescens*;
Alternaria species such as, for example, *Alternaria brassicae*;
Pseudocercosporella species such as, for example, *Pseudocercosporella herpotrichoides*. Furthermore, *Helminthosporium carbonum* may be mentioned.

The plants into which, by means of insertion (transformation) of the stilbene synthase gene or the gene unit according to the invention, resistance or increased resistance to the abovementioned pests can be introduced comprise virtually all plants. Naturally, there is a particular need for the development of resistance in the crop plants, such as forestry plants, for example spruce, fir, douglas fir, pine, larch, beech and oak, and also plants providing food and raw materials, for example, cereals (in particular wheat, rye, barley, oats, millet, rice and corn), potato, legumes such as pulses and especially alfalfa, soya beans, vegetables (in particular brassicas and tomatoes), fruit (in particular apples, pears, cherries, grapes, citrus fruit, pineapples and bananas), oil palm, tea plants, cocoa and coffee plants, tobacco, sisal and cotton, and also medicinal plants, such as Rauwolfia and Digitalis. Potato, tomatoes, vine and legumes may be mentioned as being especially preferred.

As already mentioned, according to the invention the stilbene synthase gene or the gene unit are inserted in one or several copies (at identical or different points of the genome) into the natural plant genome. In plants which are already capable of synthesizing stilbene, insertion of one or more stilbene synthase genes according to the invention may lead to a considerably improved resistance behavior. If appropriate, only the structural gene according to the invention is employed, with a regulatory gene, which may be isolated from the plant at issue, being arranged upstream.

Increased resistance of the plant cells and plants transformed according to the invention is important for agriculture and forestry, for the cultivation of ornamental plants, the cultivation of medicinal plants and the breeding of plants. Also, it is advantageous to have available plant cells exhibiting increased resistances against attack by microbial pests, in particular fungi, in the cultivation of plant cells, for example for the production of pharmaceutically useful substances.

Hence, the present invention also relates to a process for the preparation of transformed plant cells (including protoplasts) and plants (including parts of plants and seeds), characterized in that (a) one or more stilbene synthase genes or gene units and/or parts of the stilbene synthase gene or the gene unit and/or DNA modified according to the invention are introduced into the genome of plant cells (including protoplasts) and if appropriate (b) complete transformed plants are regenerated from the transformed plant cells (including protoplasts) and if appropriate (c) the desired parts of plants including seeds) are obtained from the transformed plants thus obtained.

Process stages (a), (b) and (c) can be carried out in a customary manner by known processes and methods.

Transformed plant cells (including protoplasts) and plants (including parts of plants and seeds) containing one or more stilbene synthase genes or gene units and/or parts of the stilbene synthase genes or the gene units as "foreign" or "additional" DNA, and also those transformed plant cells and plants which can be obtained by the above process, are also the subject of the present invention.

The following are also parts of the present invention:
(a) use of the stilbene synthase gene or the gene unit and/or its parts, and/or the DNA modified according to the invention and/or the vectors according to the invention and/or the microorganisms transformed according to the invention for the transformation of plant cells (including protoplasts) and plants including parts of plants and seeds), and also the
(b) use of the plant cells transformed according to the invention (including protoplasts) and plants (including parts of plants and seeds) for the production of propagation material and also for the production of novel plants and their propagation material, and generally the
(c) use of the stilbene synthase gene or the gene unit according to the invention and/or its parts and/or the DNA modified according to the invention for controlling pests.

In order to insert the stilbene synthase gene or the gene unit or its parts as "foreign" or "additional" DNA into the genetic material of plants or plant cells, a number of different techniques is available. Gene transfer can be carried out by generally customary known methods, it being possible for a person skilled in the art to choose the technique suitable for each case without difficulties.

For the transfer of foreign DNA into genomes of dicotyledon and monocotyledon plants, the Ti plasmid of *Agrobacterium tumefaciens* is available as a particularly favorable vector which can be widely employed. The genetic material coding for stilbene synthase is inserted into the T-DNA of suitable Ti plasmids (for example Zambryski et al. 1983) and is transferred by inoculation of the plants, inoculation of parts of plants, or plant tissues such as, for example, of leaf discs, stalks, hypocotyls, cotyledons, meristems and tissues derived therefrom, such as, for example, secondary embryos and calli, or by co-culture of protoplasts with *Agrobacterium tumefaciens*. Alternatively, purified DNA containing the desired gene and plant protoplasts can be incubated in the presence of polycations or calcium salts and polyethylene glycol (for example, Davey et al. 1980; Hain et al., 1985; Krens et al., 1982; Paszkowski et al., 1984).

Additionally, DNA uptake may also be enhanced by an electrical field (electroporation, for example, Formm et al., 1986).

Regeneration of plants is carried out in a known fashion with the aid of suitable nutrient media (for example, Nagy and Maliga 1976).

In a preferred embodiment of the process according to the invention (according to the method of EP-A 116,718) the DNA unit consisting of (approx.) 6.7 kb from pGS 828.1, characterized by the appropriate internal EcoRI, HindIII of PstI cleavage sites (see FIG. 1), is cloned into a suitable intermediary *E. coli* vector, for example pGV 700, pGV 710, (cf. EP-A-116,718) Deblaere et al. 1986), or preferably into derivatives thereof, which additionally contain a reporter gene such as, for example nptli (Herrera-Estrella et al. 1983) or hpt (Van den Elzen et al 1986). For this purpose, the DNA section obtained from PGS 828.1 with the aid of SstI and PvuII may also be used.

The *Escherichia coli* strain AZ 4, which contains the vector pGV 710 in a form which can be readily isolated, was deposited in the Deutsche Sammlung von Mikroorganismen (DSM) (German Collection of Microorganisms), Mascheroder Weg 1b, D-3300 Braunschweig, Federal Republic of Germany, in compliance with the provisions of the Budapest Convention on international acknowledgement of the deposition of microorganisms for the purposes of patent proceedings, and has the deposit number DSM 3164.

The plasmid constructed in this manner is transferred into *Agrobacterium tumefaciens* containing for example pGV 3850 or its derivatives (Zambryski et al. 1983) by customary methods (for example, Van Haute et al. 1983). Alternatively, the stilbene synthase gene unit may be cloned in a binary vector (for example, Koncz and Schell 1986) and can be transferred into a suitable Agrobacterium strain (Koncz and Schell 1986) as described above. The resulting Agrobacterium strain containing Ithe stilbene synthase gene unit in a form which may be transferred into plants is subsequently used for plant formation.

In a further preferred embodiment, the isolated plasmid PGS 828.1 is transferred in a customary fashion by direct gene transfer into plant protoplasts (for example, Hain et al. 1985), if appropriate together with another plasmid containing a reporter gene for plant cells, for example for kanamycin resistance (for example Herrera-Estrella et al. 1983) or for hygromycin resistance (van den Elzen, 1986), preferably PLGV neo 2103 (Hain et al. 1985), PLGV 23 neo (Herrera-Estrella 1983), pMON 129 (Fraley R. T. et al., Proc. National Acad. Sci. USA 80, 4803 (1983), pAK 1003, pAK 2004 (Velten J. et al., EMBO Journ. Vol. 3, 2723 (1984) or pGSST neo 3 (pGSST3) (EP-A-189,707). The plasmid or plasmids, may be present in their circular form, preferably, however, in their linear form. If a plasmid having a reporter gene is used, kanamycin-resistant protoplasts are then examined for expression of stilbene synthase. In the other case (without reporter gene), the resulting calli are examined for expression of the stilbene synthase gene (screening by customary methods).

Transformed (transgenic) plants or plant cells are produced by known methods, for example, by transformation of leaf discs (for example, Horsch et al. 1985), by co-culture of regenerating plant protoplasts or cell cultures with *Agrobacterium tumefaciens* (for example, Marton et al. 1979, Hain et al. 1985), or by direct DNA transfection. Resulting transformed plants are identified either by selection for expression of the reporter gene, for example by in vitro-phosphorylation of kanamycin sulphate (Reiss et al. 1984; Schreier et al. 1985), or by expression of nopaline synthase (by the method of Aerts et al. 1983) or of stilbene synthase by Northern blot analysis and Western blot analysis. Stilbene synthase and the stilbenes may also be identified in a known fashion in transformed plants with the aid of specific antibodies. Stilbene synthase can also be detected by an enzyme-activity assay (Rolfs et al., Plant Cell Reports 1, 83–85, 1981).

Cultivation of transformed plants cells and also regeneration to complete plants is carried out by generally customary techniques with the aid of suitable nutrient media in each case.

Both transformed plant cells and transformed plants which contain the stilbene synthase gene or the gene unit according to the invention, and which are constituents of the present invention, exhibit a considerably higher resistance to pests, in particular phytopathogenic fungi.

In connection with the present invention, the term "plants" stands both for complete plants and parts of plants, such as leaves, seeds, tubers, cuttings etc. "Plant cells" includes protoplasts, cell lines, plant calli etc. "Propagation material" denotes plants and plant cells which can be used for propagating the transformed plants and plant cells, and thus is also part of the present invention.

In the present connection, the term "DNA sequences acting in essentially the same way" denotes that the invention also comprises modifications in which the function of the stilbene synthase gene and its parts is not impaired to the extent that stilbene synthase is no longer produced or that the regulatory part of the gene is no longer active. Appropriate modifications can be carried out by the replacement, the addition and/or the removal of DNA sections, individual codons and/or individual nucleic acids.

In the case of the microorganisms which can be used according to the invention, "mutants" and "variants" denote modified microorganisms which still contain the features essential for the execution of the invention, in particular the relevant plasmids.

The present invention is explained in more detail by means of the following exemplary embodiments:

1. Isolation of the gene for stilbene synthase

Cell cultures of groundnut plants (Arachis hypogaea) contain the gene for stilbene synthase which in particular effects the synthesis of resveratrol synthase (size of the protein 43,000 D; reaction with specific antiserum).

The groundnut cell cultures, the regulation and properties of stilbene synthase, the antiserum against the protein and the measurement of enzyme activity have been described (Rolfs, C. H., Fritzemeier, K. H., Kindl, H., Plant Cell Reports 1, 83–85, 1981; Fritzemeier, K. H., Rolfs, C. H., Pfau, J., Kindl, H., Planta 159, 25–29, 1983; Schoppner, A., Kindl, H., J. Biol. Chem. 259, 6806–6811, 1984; see also Abstract: Kindl, H., in: Biosynthesis and Biodegradation of Wood Components, Ed. Higuchi, T., Academic Press, Inc., pp. 349–377, 1985).

The following diagram summarizes the expression of the gene and the isolation of the gene for stilbene synthase. For the procedure, known methods and techniques of molecular biology were used, as they are described in detail, for example, in the following handbook: Maniatis, T., Fritsch, E. F., Sambrook, J.: Molecular Cloning: A Laboratory Manual; Cold Spring Harbor Laboratory, 1982.

A. Isolation and identification of specific cDNA clones for stilbene synthase.

Initially, poly(A)-containing RNA from groundnut cell cultures synthesizing stilbene synthase are isolated. The mRNA is then transcribed into DNA with the aid of reverse transcriptase and *E. coli* DNA polymerase; the DNA is cloned in plasmid vector pINIIA with the aid of linkers and multiplied in *E. coli* strain JA221 (Nakamura, K., Inouye, M., EMBO J. 1, 771–775, 1982). This process results in a "cDNA library": it represents the mRNA population of the groundnut cells, cloned as DNA in *E. coli* plasmids. It contains the nucleic acid coding for stilbene synthase, and this is identified by the following steps:

(i) the specific cDNA hybridizes with stilbene synthase mRNA, (ii) by hybridization with cDNA, an mRNA is isolated which, on in vitro translation, results in a protein identical with stilbene synthase (protein size 43,000 D; reaction of the protein with antiserum which reacts specifically with stilbene synthase protein).

On the cDNA level, these criteria define unequivocally the nucleic acid which codes for the stilbene synthase protein.

B. Isolation of the gene for stilbene synthase.

Initially, a "gene library" for groundnut cells is established: genomic DNA from enriched cell nuclei (Bedbrook, J., Plant Molecular Biology Newsletter 2, 24, 1981) is cleaved with the restriction enzyme SauIIIa such that DNA fragments having an average length of 10,000–25,000 nucleotide pairs are formed. These fragments are cloned into the BamHI site of Lambda phage EMBL3 (Frischauf et al., J. Mol. Biol. 170, 827–842, 1983), and the phages are multiplied in *E. coli*. The whole of the phage population contains, cloned in segments, the complete genomic DNA of the groundnut cells, and thus also the gene for stilbene synthase.

The gene for stilbene synthase, its mRNA and the stilbene synthase cDNA contain the same nucleic acid sequences, because they are derived from each other

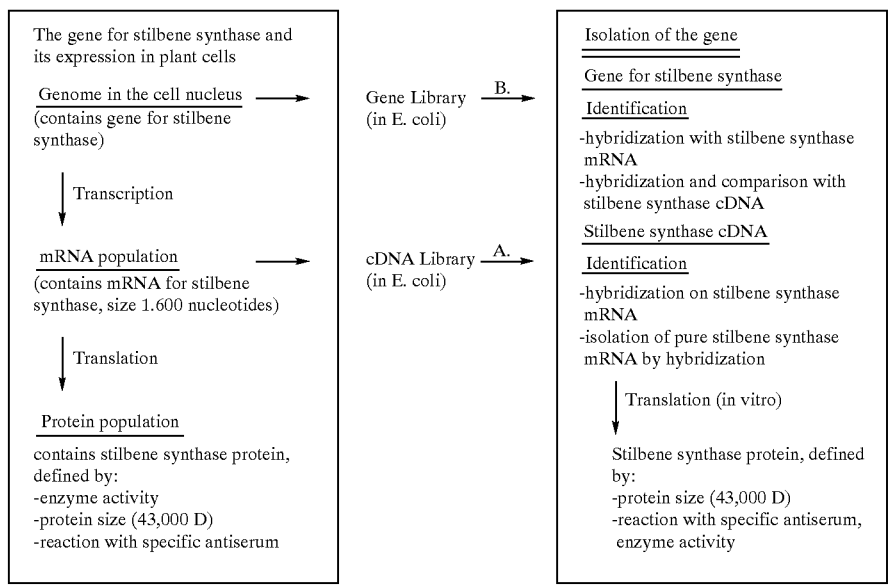

Diagram for the expression of the stilbene synthase gene and for its isolation from plant cells (gene→mRNA→cDNA). This means that the gene for stilbene synthase can be identified by specific hybridization with stilbene synthase cDNA or stilbene synthase mRNA. The phages containing the gene are identified by hybridization and then isolated and multiplied. The genomic DNA from groundnut cells cloned in this phage is mapped further by analysis with various restriction enzymes, and the position of the stilbene synthase gene is located by further hybridization experiments with cDNA. Finally, the gene unit is cleaved from the phage by partial digestion with EcoRI and HindIII, cloned in the correspondingly cleaved plasmid vector pSP65 (from Amersham Buchler GmbH & Co KG, Brunswick, Federal Republic, of Germany), and is multiplied as a recombinant plasmid. This plasmid is called pGS 828.1.

2. Description of the plasmid pGS 828.1 (cf. FIG. 1–FIG. 2)

The plasmid consists of two components:

(i) gene unit stilbene synthase: the complete gene, consisting of the structural gene and regulator moiety (both from groundnut cells) is on a nucleic acid which is cleaved from the plasmid as a DNA fragment of (approx.) 6700 nucleotide pairs by partial cleavage with the restriction enzymes EcoRI and HindIII. The gene unit contains cleavage sites for the restriction enzymes EcoRI, HindIII and PstI.

(ii) Vector plasmid: the gene unit is cloned in vector pSP65. The size of the vector is 3,000 nucleotide pairs. It carries the gene for ampicillin resistance, i.e., $E.$ $coli$ cells containing this plasmid grow in nutrient media which contain the antibiotic ampicillin. Ori: name for sequences which are necessary for multiplication of the plasmid in $E.$ $coli.$ The plasmid carries a gene for ampicillin resistance and contains 9,350 nucleotide pairs (9.35 kBp). It can be multiplied in $E.$ $coli$ cells containing pGS 828.1 ($E.$ $coli$ Nurdug 2010) in a customary fashion.

Preferred nutrient medium for $E.$ $coli$ cells (for example JA221, Nakamura, K., Inouye, M., EMBO J. 1, 771–775, 1982) containing pGS 828.1 ($E.$ $coli$ Nurdug 2010):

| | | |
|---|---|---|
| Bacto peptone* | 10 | g |
| yeast extract | 5 | g |
| NaCl | 5 | g |
| agar | 20 | g |
| H₂O | 1 | l |
| pH 7.5 | | |
| fermentation: 37° C., aerobic | | |

(*Bacto is a trademark of DIFCO Lab. Detroit, USA).

3. Transformation of tobacco a) culture of tobacco shoots and isolation of tobacco protoplasts:

Nicotiana tabacum (Petit Havanna SR1) is propagated as a sterile shoot culture on hormone-free LS medium (Linsmaier and Skoog 1965). Every 6–8 weeks, approximately, shoot segments are transferred to fresh LS medium. The shoot cultures are kept in a growth chamber with 12 h light (1,000–3,000 lux) at 24–26° C.

For the isolation of leaf protoplasts, approx. 2 g of leaves (approx. 3–5 cm long) are cut into small pieces (0.5 cm×1 cm) using a new razor blade. The leaf material is incubated at room temperature in 20 ml of enzyme solution consisting of K3 medium (Nagy and Maliga 1976), 0.4 M sucrose, pH 5.6, 2% cellulase R10 (Serva) and 0.5% Macerozyme R10 (Serva) for 14–16 hours.

After this, the protoplasts are separated from cell debris by filtration, using 0.30 mm and 0.1 mm steel sieves. The filtrate is centrifuged for 10 minutes at 100×g. During this centrifugation, intact protoplasts float and gather in a band at the upper margin of the enzyme solution. The pellet of cell debris and the enzyme solution are removed by suction using a glass capillary. The prepurified protoplasts are made up to 10 ml with fresh K3 medium (0.4 M sucrose as osmoticallyactive constituent), and floated again. The washing medium is removed by suction, and the protoplasts are diluted to $1-2\times10^5$/ml for culture or for following inoculation with Agrobacteria (co-culture). The concentration of protoplasts is determined in a counting cell.

b) Transformation of regenerating tobacco protoplasts by co-culture with $Agrobacterium$ $tumefaciens:$ In the following, the method of Marton et al. 1979 is used, slight alterations being made. The protoplasts are isolated as described and are incubated at a density of $1-2\times10^5$/ml in K3 medium (0.4 M sucrose, 0.1 mg/l NAA, 0.2 ml in K3 medium (0.4 M sucrose, 0.1 mg/l NAA, 0.2 mg of kinetin) for 2 days in the dark and for one to two days in dim light (500 lux) at 26° C. As soon as the first divisions of protoplast are visible, 30 μl of an Agrobacterium suspension in minimal A (Am)-medium (density approx. $10^9$ Agrobacteria/ml) are added to 3 ml of regenerating protoplasts. The duration of co-culture is 3–4 days at 20° C. in the dark. After this, the tobacco cells are transferred into 12 ml centrifuge tubes, diluted with seawater (600 mOsm/kg) to 10 ml, and pelleted at 60×g for 10 minutes. This washing procedure is repeated another 1–2 times, in order to remove the majority of the Agrobacteria. The cell suspension is cultivated in a density of $5\times10^4$/ml in K3 medium (0.3 M sucrose) containing 1 mg/l NAA (naphthyl-1-acetic acid), 0.2 mg/l kinetin and 500 mg/l of the cephalosporin antibiotic cefotaxime. Each week, the cell suspension is diluted with fresh K3 medium, and the osmotic value of the medium is gradually reduced by 0.05 M sucrose (approx. 60 mOsm/kg) per week. Selection with kanamycin (100 mg/l kanamycin sulphate (Sigma), 660 mg/g of active km) is started 2–3 weeks after the co-culture in agarose bead type culture (Shillito et al. 1983). Kanamycin-resistant colonies can be distinguished 3–4 weeks after the beginning of selection from the background of retarded colonies.

c) Direct transformation of tobacco protoplasts with DNA. Calcium nitrate/PEG transformation In a Petri dish, approximately $10^6$ protoplasts in 180 μl of K3 medium are mixed carefully with 20 μl of aqueous DNA solution containing 0.5 μg/μl pGS 828.1 and 0.5 μg/μl PLGV neo 2103 (Hain et al. 1985). Subsequently, 200 μl of fusion solution (0.1 M calcium nitrate, 0.45 M mannitol, 25% polyethylene glycol (PEG 6000), pH 9) are carefully added. After 15 minutes, 5 ml of washing solution (0.275 M calcium nitrate pH 6) are added, and after a further 5 minutes the protoplasts are transferred to a centrifuge tube and pelleted at 60×g. The pellet is taken up in a small amount of K3 medium and is cultivated as described in the following passage. Alternatively, the protoplasts may be transformed as by Hain et al. 1985.

Alternatively, the transformation can be carried out without the addition of the 0.5 μg/μl pLGV neo 2103. Since no reporter gene is employed in this case, the resulting calli are screened for the presence of the stilbene synthase gene unit with the aid of a dot-blot hybridization. An internal EcoRI-HindIII fragment from pGS 828.1 may be used as the hybridization probe.

Other identification methods, such as an antibody assay or determination of a fungicide resistance can, of course, also be used.

d) Culture of the protoplasts incubated with DNA and selection of kanamycin-resistant calli:

For the culture and selection of kanamycin-resistant colonies described below, a modified "bead type culture" technique (Shillito et al. 1983) is used. One week after treatment of the protoplasts with DNA (cf. c), 3 ml of the cell suspension are mixed with 3 ml of K3 medium (0.3 M sucrose+hormones; 1.2% (sea-plaque) LMT agarose (low melting agarose, Marine Colloids) in 5 cm Petri dishes. For this purpose, agarose is dry autoclaved and, after K3 medium has been added, briefly brought to the boil in a microwave oven. After the agarose has solidified, the agarose discs ("beads") containing the embedded tobacco microcalli are transferred into 10 cm Petri dishes for further culture and selection, and to each is added 10 ml of K3 medium (0.3 M sucrose, 1 mg/l NAA, 0.2 mg/l kinetin) and 100 mg/l kanamycin sulphate (Sigma). The aliquid medium is changed each week. In the course of this, the osmotic value of the medium is reduced stepwise. The replacement medium (K3+Km) is reduced by 0.05 M sucrose (approx. 60 mOsm) per week.

Scheme for the selection of kanamycin-resistant tobacco colonies after DNA transformation:

| A | E | 0.4M S | 0.3M | 0.25M | 0.20M | 0.15M K | 0.10M | Sucrose in liquid medium |
|---|---|---|---|---|---|---|---|---|
|   |   | 1 | 2 | 3 | 4 | 5 | 6 | weeks after DNA uptake |
|   |   |   |   | (K3 medium 1 mg NAA, 0.2 mg kinetin) |   |   |   |   |

A = DNA uptake
E = embedding in agarose
S = selection with kanamycin (100 mg/l kanamycin sulphate)
K = kanamycin-resistant colonies can be distinguished unequivocally from the background e) Regeneration of kanamycin-resistant plants:

As soon as the kanamycin-resistant colonies have reached a diameter of approximately 0.5 cm, half of them are put onto regeneration medium (LS medium, 2% sucrose, 0.5 mg/l benzylaminopurine BAP) and are kept in a growth cabinet with 12 hours of lilht (3,000–5,000 lux) at 24° C. The other half is propagated as a callus culture on LS medium containing 1 mg/l NAA, 0.2 mg/l kinetin, 0.1 mg/l BAP and 100 mg/l kanamycin sulphate. As soon as the regenerated shoots are approx. 1 cm in length, they are cut off and placed onto ½ LS medium (1% sucrose, 0.8% agar) without growth regulators for rooting. The shoots are rooted on ½ MS medium containing 100 mg/l kanamycin sulphate and are later transferred to soil.

f) Transformation of leaf discs by *Agrobacterium tumefaciens*

For the transformation of leaf discs (Horsch et al. 1985), discs of 1 cm diameter are cut out of approx. 2–3 cm long leaves of sterile shoot cultures and incubated with a suspension of the relevant Agrobacteria (approx. $10^9$/ml) (cf. b) in Am medium, see below) for approx. 5 minutes. The infected leaf discs are kept on MS medium (see below) without hormones for 3–4 days at approx. 24° C. During this time, Agrobacterium overgrows the leaf discs. The leaf discs are then washed in MS medium (0.5 mg/ml BAP, 0.1 mg/ml NAA) and put on the same medium (0.8% agar) containing 500 µg/ml cefotaxim and 100 µg/ml kanamycin sulphate (Sigma). The medium should be renewed after two weeks. Transformed shoots are visible after a further 2–3 weeks. The regeneration of shoots without selection pressure should also be carried out in parallel. The regenerated shoots then have to be tested for transformation by biological assays for, for example, nopaline synthase or stilbene synthase activity. In this manner, 1–10% of transformed shoots are obtained.

Biochemical method for detection of transformation Detection of nopaline in plant tissues:

Nopaline is detected as described by Otten and Schilperoort (1978) and Aerts et al. (1979), as follows. 50 mg of plant material (callus or leaf discs) are incubated in LS medium containing 0.1 M arginine in an Eppendorf tube at room temperature overnight. The plant material is then dried by dabbing on absorbent paper, homogenized in a new Eppendorf centrifuge tube with the aid of a glass rod, and centrifuged in an Eppendorf centrifuge for 2 min. 2 µl of the supernatant are applied, in the form of small dots, to paper suitable for electophoresis (Whatman 3 MM paper) (20×40 cm) and the paper is dried. The paper is impregnated with the solvent (5% formic acid, 15% acetic acid, 80% $H_2O$, pH 1.8), and electrophoresis is carried out at 400 V for 45 minutes. Nopaline migrates towards the cathode. The paper is then dried in a stream of hot air and drawn through phenanthrenequinone dye (equal volume of 0.02% phenanthrenequinone in ethanol and 10% NaOH in 60% ethanol) in the direction of migration. The dried paper is inspected under long-wavelength UV light, and photographed. Arginine and arginine derivatives are dyed with the reagent to give a yellow fluorescence.

Neomycin phosphotransferase (NPT II) enzyme assay: NPT II activity in plant tissue is detected by in situ phosphorylation of kanamycin, as described by Reiss et al. (1984) and as modified by Schreier et al. (1985), as follows. 50 mg of plant tissue are homogenized in 50 µl of extraction buffer (10% glycerol, 5% 2-mercaptoethanol, 0.1% SDS, 0.025% bromophenol blue and 62.5 mM Tris pH 6.8) with the addition of ground glass and immersed in ice, and the mixture is centrifuged for 10 minutes in an Eppendorf centrifuge at 40° C. 50 µl of the supernatant are applied to a non-denaturing polyacrylamide gel (145×110×1.2 mm; separation gel: 10% acrylamide, 0.33% bisacrylamide and 0.375 M Tris pH 8.8, collecting gel: 5% acrylamide, 0.165% of bisacrylamide and 0.125 M Tris pH 6.8), and electrophoresis is carried out overnight at 4° C. and at 60 V. As soon as the bromophenol blue marker runs out of the gel, the gel is washed twice for 10 minutes with distilled water and once for 30 minutes with reaction buffer (67 mM Tris maleate, pH 7.1, 42 mM $MgCl_2$ and 400 mM ammonium chloride). The gel is transferred onto a glass plate of the same size and covered with a layer of 40 ml of 1% strength agarose in reaction buffer containing the substrates kanamycin sulphate (20 µg/ml) and 20–200 µCi $^{32}$p ATP (Amersham). The sandwich gel is incubated at room temperature for 30 minutes, and then a sheet of P81 phosphocellulose paper (Whatman) is put onto the agarose. Four layers of 3 MM filter paper, (Whatman) and a few paper towels are stacked over this. The transfer of in situ-phosphorylated radioactive kanamycin phosphate to the P81 paper is stopped after 3–4 hours. The P81 paper is incubated for 30 minutes in a solution of proteinase K and 1% sodium dodecyl sulphate (SDS) at 60° C., is then washed 3–4 times in 250 ml of 10 mM phosphate buffer pH 7.5 at 80° C., dried and autoradiographed for 1–12 hours at −70° C. (XAR5 Kodak film).

4. Transformation of Medicago sativa (lucerne)

a) Plant material

The plant Medicago sativa (regen S, clone $RA_3$, Walker et al., 1978) was cultured as a sterile shoot culture on LS medium (Linsemaier and Skoog, 1965) under long-day conditions (16 h light, 8 h dark) at 26±2° C.

b) Culture conditions

Glass containers (250 ml to 1.5 l) provided with loose glass lids were used as culture containers. Plastic Petri dishes were used for all the other plant cultures (embryo, callus, protoplasts).

The plants and tissue cultures, except for the protoplasts, were cultured in growth chambers under long-day conditions (16 hours liaht, 8 hours dark) at 26±2° C. The fluorescent tubes had the light color Universal Weiss (Osram L58W/25). The distance of the tubes to the cultures was 10 to 30 cm, equivalent to 1500–4500 lux light intensity. Air humidity was not regulated. The protoplasts were cultured in incubators at not more than 500 lux and 26° C.

c) Callus culture

Callus was induced from petioles of greenhouse plants. Petiole sections of approx. 5 cm length were dissected from the greenhouse plants by means of a scalpel. First, the petiole sections were surface-sterilized:

1 min in 70% strength ethanol 10 min in 10% strength of a commercially available disinfectant (for example Dan Klorix)

3 rinses in sterile tap water.

After sterilization, the petiole sections were cut into sections of 1–1.5 cm length and placed on solid agar medium in Petri dishes. Three different media were used for callus induction and further culture:

1. $B_5h$ (Atanassov and Brown, 1984)
2. SHG: SH (Schenk and Hildebrandt, 1972) containing 25 $\mu M$ (4.655 mg/l) of NAA and 10 $\mu M$ (2.15 mg/l) of kinetin (Walker and Sato, 1981)
3. $B_5H_3$: $B_5$ (Gamborg et al., 1968) containing 2.6 $\mu M$ (0.5 mg/l) of NAA, 2.2 $\mu M$ (0.5 mg/l) of BAP, 2.2 $\mu M$ (0.5 mg/l) of 2,4 D (Oelck, Phd thesis 1984).

After three weeks, the outer parts of the callus were cut off in each case by means of a scalpel and subcultured on fresh medium.

d) Callus regeneration

The regeneration of plants from callus was carried out following a modified protocol by Stuart and Strickland, 1984 a, b.

Somatic embryogenesis was induced by incubating callus tissue in liquid SH medium (Schenk and Hildebrandt, 1972) containing 50 $\mu M$ (11 mg/l) of 2,4 D and 5 $\mu M$ (1.07 mg/l) of kinetin. 30 mg of callus (fresh weight) were added per ml of medium, contained in a conical flask (100 ml in a 500 ml flask). Induction was effected by placing the culture for 3–4 days on a rotary shaker (100 rpm) in a plant growth chamber at 26° C. The callus tissue was then separated from the medium on a sieve (850 $\mu m$).

The tissue was squeezed through the sieve by means of a spatula, and small cell lumps were collected on a sieve of mesh size 250 $\mu m^2$ which was placed under the sieve. The cell lumps were washed with 500 ml of SHJ medium without hormones (SH) per 100 ml of induction medium. As much as possible of the washing solution was removed by dripping off (approx. 5 minutes). The fresh weight was determined, and the cell lumps were resuspended in SH medium. 75 mg in 0.5 ml were pipetted onto approx. 10 ml of solid regeneration medium SHR. The regeneration medium SHR consisted of SH medium containing 25 mM of $NH_4+$ and 100 mM of L-proline and 3% of sucrose.

Approx. four weeks later, well developed embryos showing distinct polarity (cotyledon stage, Dos Santos et al., 1983) were placed on solid ½Z SH medium containing 25 $\mu M$ (8.6 mg/l) of gibberellic acid ($GA_3$) and 0.25 $\mu M$ (0.046 mg) of NAA. After root formation and the development of a shoot with leaves the young plantlets were transferred to LS medium.

The composition of media $B_5h$, SHJ, SHR, ½ SH and LS is indicated in the table. The liquid SH medium is equivalent to SHJ medium without the hormones 2,4D and kinetin. Unless otherwise stated, amounts are given in mg/l.

| | $B_5h$ | SHJ | SHR | ½SH | LS |
|---|---|---|---|---|---|
| Macroelements | | | | | |
| $NH_4NO_3$ | — | — | — | — | 1650 |
| $KNO_3$ | 3000 | 2500 | 2500 | 1250 | 1900 |
| $CaCl_2\ 2H_2O$ | 895 | 200 | 200 | 100 | 1900 |
| $MgSO_4\ 7H_2O$ | 500 | 400 | 400 | 200 | 370 |
| $(NH_4)_2SO_4$ | 134 | — | 1651 | — | — |
| $NaH_2PO_4H_2O$ | 156 | — | 407 | — | — |
| $KH_2PO_4H_2O$ | — | — | — | — | 170 |
| $NH_4H_2PO_4$ | — | 300 | — | 150 | — |
| Microelements | | | | | |
| $ZnSO_4H_2O$ | 10 | 10 | 10 | 5 | 22.3 |
| $H_3BO_3$ | 3 | 5 | 5 | 2.5 | 6.2 |
| $ZnSO_4\ 7H_2O$ | 1 | 1 | 1 | 0.5 | 8.6 |
| $Na_2MoO_4\ 2H_2O$ | 0.25 | 0.1 | 0.1 | 0.05 | 0.25 |
| $CuSO_4\ 5H_2O$ | 0.025 | 0.02 | 0.02 | 0.1 | 0.025 |
| $CaCl_2\ 6H_2O$ | 0.025 | 0.1 | 0.1 | 0.05 | 0.025 |
| KJ | 0.75 | 1 | 1 | 0.5 | 0.83 |
| $FeSO_4\ 7H_2O$ | 28 | 15 | 15 | 7.5 | 28 |
| $Na_2$ EDTA | 37 | 20 | 20 | 10 | 37 |
| Vitamins | | | | | |
| Thiamine HCl | 10 | 5 | 5 | 2.5 | 0.4 |
| Pyridoxine HCl | 1 | 0.5 | 0.5 | 0.25 | — |
| Nicotinic acid | 1 | 5 | 5 | 2.5 | — |
| Amino acids | | | | | |
| L-Glutamine | 800 | — | — | — | — |
| L-Serine | 100 | — | — | — | — |
| L-Proline | — | — | 5755 | — | — |
| Other constituents among others, plant hormones | | | | | |
| Myo-inositol | 100 | 1000 | 1000 | 500 | 100 |
| L-Glutathione | 10 | — | — | — | — |
| Adenine sulphate | 1 | — | — | — | — |
| 2,4D | 1 | 11.5 | — | — | — |
| Kinetin | 0.2 | 1.075 | — | — | — |
| $GA_3$ | — | — | — | 8.6 | — |
| NAA | — | — | — | 0.046 | — |
| Sucrose | 30 g | 30 g | 30 g | 15 g | 10 g |
| pH | 5.8 | 5.9 | 5.9 | 5.9 | 5.8 |

The pH was adjusted with 1N KOH.

The media were sterilized by autoclaving for 17 min at 121° C. Kinetin, L-glutathione and the amino acids were filter-sterilized and added to the medium of a temperature of 60° C., after autoclaving.

e) Protoplast culture

The leaves of sterile shoot cultures of an age of 2–3 month were used as starting material for the isolation of protoplasts. The leaves were harvested 2–3 hours after switching on the light.

First, the leaves, contained in a Petri dish, were wetted with EMI (Atanassov and Brown, 1984) and cut into small pieces using a new razor blade.

Approx. 1–1.5 g of leaves were then incubated in a Petri dish (10 cm diameter) with 10 ml of enzyme solution for 3–4 hours. Incubation was carried out at 26° C. and dim light. Liberation of the protoplasts from the leaves was monitored under the microscope. The dish was swirled 2–3 times every 30 minutes.

The enzyme solution consisted of a 1:1 mixture of the protoplast culture medium (AP) by Atanassov and Brown (1984) containing the hormones 2,4D (0.2 mg/l), zeatin (0.5 mg/l) and NAA (1 mg/l), and an enzyme solution. The enzyme solution (Kao and Michayluk, 1979; modified) consisted of:

| | |
|---|---|
| 200 mg | of cellulase Onozuka R10 |
| 80 mg | of Macerozyme R10 Serva |
| 10 mg | of Pectolyase Y-23 Sigma |
| 540 mg | of Sorbitol | f) Transformation of an induced callus

Callus was induced to embryogenesis by the method described under callus regeneration.

Following 3–4 days' incubation in liquid SHJ, the callus material was rinsed on a sieve (mesh size 100 μm) with liquid SHR which did not contain agar or L-proline. The callus material was then taken up in liquid SHR. Approx. 1 g of callus material was added to 10 ml of medium.

Agrobacteria containing stilbene synthase gene-carrying Ti plasmids were added ($2 \times 10^7$/ml final concentration), and the callus material was incubated for 2–3 days on a rotary shaker (90 rpm) at 26° C.

The material was then rinsed on a sieve (mesh size 100 μm) with liquid SHR.

For plating (75 mg of callus/10 ml of medium), customary solid SHR containing 100 mM L-proline was used. In addition to the selective antibiotics, the medium in the plates contained 500 μg/ml of claforan. Four weeks later, the resistant structures were transferred to fresh medium containing antibiotics, and a further three weeks later they were divided and half of them was transferred onto fresh medium without selective antibiotics, half of them onto medium containing antibiotics.

g) Transformation of embryos

Transformation of embryos was carried out in analogy to transformation of the induced callus. 4–5-Weeks-old embryos were used as starting material. With a razor blade, they were cut into small pieces in a Petri dish and then rinsed on a sieve (mesh size 100 $\mu m^2$) with liquid SHR. Approx. 1 g of cut embryos were taken up in 10 ml of liquid SHR. Agrobacteria were added ($2 \times 10^7$/ml final concentration), and the cultures were incubated for 2–3 days on a rotary shaker (90 rpm) at 26° C. The embryo pieces were then rinsed on a sieve (100 μm) with liquid SHR. Plating was carried out on plates containing the customary solid SHR and 100 mM of L-proline, by means of a spatula. Approx. 50–100 mg of embryo pieces were distributed per 10 ml medium plate. In addition to the selective antibiotics, the medium in the plates contained 500 μg/ml of claforan. Three weeks after plating, the secondary embryos were subcultured on fresh plates. Well developed embryos were transferred to antibiotics-free ½ SH medium (Stuart and Strickland, 1984 a, b) to facilitate further development into plants. Small rooted plantlets were then transferred to LS medium.

5. Transformation of Solanum tuberosum (potato)

Transformation was carried out exactly in the manner indicated in EP-A-0,242,246, pages 14 to 15, the Agrobacteria containing Ti plasmids carrying the stilbene synthase gene.

Unless otherwise stated, all the data in the above examples given in per cent refer to per cent by weight.

In the plant cells and plants (tobacco) obtained according to the above examples, the presence of the stilbene synthase gene was confirmed by Southern blot analysis. The expression of the stilbene synthase gene was detected by Northern blot analysis, and stilbene synthase and stilbenes were detected with the aid of specific antibodies. Transformed and non-transformed plants (for comparison) were sprayed with a spore suspension of Botrytis cinera, and fungal attack was rated after 1 week. The transformed plants showed (as opposed to the non-transformed comparison plants) an increased resistance to fungal attack. Corresponding positive results were obtained for Medicago sativa and potato.

The DNA sequence (protein-encoding region and intron) of the stilbene synthase gene including a proportion of the 5'- and 3'-untranslated regions, as it is present in plasmid pGS 828.1, is given below. The restriction cleavage sites for EcoRI, PstI and HindIII are indicated. The corresponding protein sequence is given in the one-letter code.

```
                                                         E
                                                         c
                                                         o
                                                         R
                                                         I
      cacagctaagaaaagATGGTGTCTGTGAGTGGAATTCGCAAGGTTCAAAGGGCAGAAGGT
  1   ---------+---------+---------+---------+---------+---------+ 60
      gtgtcgattcttttcTACCACAGACACTCACCTTAAGCGTTCCAAGTTTCCCGTCTTCCA

M  V  S  V  S  G  I  R  K  V  Q  R  A  E  G  -

CCAGCAACGGTATTGGCGATCGGAACAGCAAATCCACCAAACTGTGTTGATCAGAGTACA
  61  ---------+---------+---------+---------+---------+---------+ 120
      GGTCGTTGCCATAACCGCTAGCCTTGTCGTTTAGGTGGTTTGACACAACTAGTCTCATGT

P  A  T  V  L  A  I  G  T  A  N  P  P  N  C  V  D  Q  S  T  -

TATGCAGATTATTATTTTAGAGTAACCAACGGCGAACACATGACTGATCTCAAGAAGAAA
 121  ---------+---------+---------+---------+---------+---------+ 180
      ATACGTCTAATAATAAAATCTCATTGGTTGCCGCTTGTGTACTGACTAGAGTTCTTCTTT
```

-continued

```
            Y  A  D  Y  Y  F  R  V  T  N  G  E  H  M  T  D  L  K  K  K  -

TTTCAGCGCATCTgtatgtatttttattaagcgttctatatttgtttatatttaatattt
  181 ---------+---------+---------+---------+---------+---------+ 240
      AAAGTCGCGTAGAcatacataaaaataattcgcaagatataaacaaatataaattataaa

F  Q  R  I  C atcaaaataaaattcgttcttttattttatattaattaatacaggaataatttaacata
  241 ---------+---------+---------+---------+---------+---------+ 300
      tagttttattttaagcaagaaaataaaaatataattaattatgtccttattaaattgtat ttatatacaacatatcatattggctacttaatattaacaataataattacttaataataa
  301 ---------+---------+---------+---------+---------+---------+ 360
      aatatatgttgtatagtataaccgatgaattataattgttattattaatgaattattatt attatttcaatagttataaaataaattatttcaattcttatacatttggataaactatta
  361 ---------+---------+---------+---------+---------+---------+ 420
      taataaagttatcaatattttatttaataaagttaagaatatgtaaacctatttgataat aaataatgagacatgaacgttcaagttactataaaaataactcaaaaataacattattat
  421 ---------+---------+---------+---------+---------+---------+ 480
      tttattactctgtacttgcaagttcaatgatattttttattgagttttattgtaataata tgatatgtgtgtgtatgtgtatgtcgttttctaaatgtcatcaagggtattgatggatg
  481 ---------+---------+---------+---------+---------+---------+ 540
      actatacacacacatacacatacagcaaaaagatttacagtagttcccataactacctac tgaatttcatattattatttcagGTGAGAGAACACAGATCAAGAATAGACATATGTACTT
  541 ---------+---------+---------+---------+---------+---------+ 600
      acttaaagtataataataaagtcCACTCTCTTGTGTCTAGTTCTTATCTGTATACATGAA
                             E  R  T  Q  I  K  N  R  H  M  Y  L AACAGAAGAGATACTGAAAGAGAACCCTAACATGTGCGCATATAAGGCACCGTCGTTGGA
  601 ---------+---------+---------+---------+---------+---------+ 660
      TTGTCTTCTCTATGACTTTCTCTTGGGATTGTACACGCGTATATTCCGTGGCAGCAACCT

T  E  E  I  L  K  E  N  P  N  M  C  A  Y  K  A  P  S  L  D  -

TGCAAGAGAAGACATGATGATCAGGGAGGTACCAAGGGTTGGAAAAGAGGCTGCAACCAA
  661 ---------+---------+---------+---------+---------+---------+ 720
      ACGTTCTCTTCTGTACTACTAGTCCCTCCATGGTTCCCAACCTTTTCTCCGACGTTGGTT

A  R  E  D  M  M  I  R  E  V  P  R  V  G  K  E  A  A  T  K  -

GGCCATCAAGGAATGGGGCCAGCCAATGTCTAAGATCACACATTTGATCTTCTGCACCAC
  721 ---------+---------+---------+---------+---------+---------+ 780
      CCGGTAGTTCCTTACCCCGGTCGGTTACAGATTCTAGTGTGTAAACTAGAAGACGTGGTG

A  I  K  E  W  G  Q  P  M  S  K  I  T  H  L  I  F  C  T  T  -

CAGCGGCGTTGCGTTGCCTGGCGTTGATTATGAACTCATCGTACTCTTAGGGCTCGACCC
  781 ---------+---------+---------+---------+---------+---------+ 840
      GTCGCCGCAACGCAACGGACCGCAACTAATACTTGAGTAGCATGAGAATCCCGAGCTGGG

S  G  V  A  L  P  G  V  D  Y  E  L  I  V  L  L  G  L  D  P  -

AAGTGTCAAGAGGTACATGATGTACCACCAAGGTTGCTTTGCTGGTGGCACTGTCCTTCG
  841 ---------+---------+---------+---------+---------+---------+ 900
      TTCACAGTTCTCCATGTACTACATGGTGGTTCCAACGAAACGACCACCGTGACAGGAAGC

S  V  K  R  Y  M  M  Y  H  Q  G  C  F  A  G  G  T  V  L  R  -

TTTGGCTAAGGACTTGGCAGAAAACAACAAGGATGCTCGTGTGCTTATTGTTTGTTCTGA
  901 ---------+---------+---------+---------+---------+---------+ 960
      AAACCGATTCCTGAACCGTCTTTTGTTGTTCCTACGAGCACACGAATAACAAACAAGACT

L  A  K  D  L  A  E  N  N  K  D  A  R  V  L  I  V  C  S  E  -
                                 P
                                 s
                                 t
                                 I
      GAATACTGCAGTCACTTTTCGTGGTCCTAATGAGACAGACATGGATAGTCTTGTAGGGCA
  961 ---------+---------+---------+---------+---------+---------+ 1020
      CTTATGACGTCAGTGAAAAGCACCAGGATTACTCTGTCTGTACCTATCAGAACATCCCGT

N  T  A  V  T  F  R  G  P  N  E  T  D  M  D  S  L  V  G  Q  -

AGCATTGTTTGCCGATGGAGCTGCTGCAATTATCATTGGTTCTGATCCTGTTCCAGAGGT
```

```
                                      -continued
1021 ---------+---------+---------+---------+---------+---------+ 1080
     TCGTAACAAACGGCTACCTCGACGACGTTAATAGTAACCAAGACTAGGACAAGGTCTCCA A   L   F   A   D   G   A   A   A   I   I   I   G   S   D   P   V   P   E   V   -

TGAGAATCCTCTCTTTGAGATTGTTTCAACTGATCAACAACTTGTCCCTAACAGCCATGG
1081 ---------+---------+---------+---------+---------+---------+ 1140
     ACTCTTAGGAGAGAAACTCTAACAAAGTTGACTAGTTGTTGAACAGGGATTGTCGGTACC

E   N   P   L   F   E   I   V   S   T   D   Q   Q   L   V   P   N   S   H   G   -

AGCCATCGGTGGTCTCCTTCGTGAAGTTGGACTTACATTTTATCTTAACAAGAGTGTTCC
1141 ---------+---------+---------+---------+---------+---------+ 1200
     TCGGTAGCCACCAGAGGAAGCACTTCAACCTGAATGTAAAATAGAATTGTTCTCACAAGG

A   I   G   G   L   L   R   E   V   G   L   T   F   Y   L   N   K   S   V   P   -

H
                                                    i
                                                    n
                                                    d
                                                    I
                                                    I
                                                    I
     GGATATTATTTCACAAAACATCAATGGTGCACTCAGTAAAGCTTTTGATCCACTGGGTAT
1201 ---------+---------+---------+---------+---------+---------+ 1260
     CCTATAATAAAGTGTTTTGTAGTTACCACGTGAGTCATTTCGAAAACTAGGTGACCCATA

D   I   I   S   Q   N   I   N   G   A   L   S   K   A   F   D   P   L   G   I   -

ATCTGATTATAACTCAATATTTTGGATTGCACATCTTGGTGGACGCGCAATTTTGGACCA
1261 ---------+---------+---------+---------+---------+---------+ 1320
     TAGACTAATATTGAGTTATAAAACCTAACGTGTAGAACCACCTGCGCGTTAAAACCTGGT

S   D   Y   N   S   I   F   W   I   A   H   L   G   G   R   A   I   L   D   Q   -

AGTTGAACAGAAGGTGAACTTGAAGCCAGAGAAGATGAAAGCCACTAGAGATGTACTTAG
1321 ---------+---------+---------+---------+---------+---------+ 1380
     TCAACTTGTCTTCCACTTGAACTTCGGTCTCTTCTACTTTCGGTGATCTCTACATGAATC

V   E   Q   K   V   N   L   K   P   E   K   M   K   A   T   R   D   V   L   S   -

CAATTATGGTAACATGTCAAGTGCGTGTGTGTTCTTCATTATGGATTTGATGAGAAAGAA
1381 ---------+---------+---------+---------+---------+---------+ 1440
     GTTAATACCATTGTACAGTTCACGCACACACAAGAAGTAATACCTAAACTACTCTTTCTT

N   Y   G   N   M   S   S   A   C   V   F   F   I   M   D   L   M   R   K   K   -

GTCACTTGAAACTGGACTTAAAACCACTGGAGAAGGACTTGATTGGGGTGTGTTGTTTGG
1441 ---------+---------+---------+---------+---------+---------+ 1500
     CAGTGAACTTTGACCTGAATTTTGGTGACCTCTTCCTGAACTAACCCCACACAACAAACC

S   L   E   T   G   L   K   T   T   G   E   G   L   D   W   G   V   L   F   G   -

TTTTGGCCCTGGTCTCACTATTGAAACCGTTGTTCTCCGCAGCATGGCCATAtaatacgc
1501 ---------+---------+---------+---------+---------+---------+ 1560
     AAAACCGGGACCAGAGTGATAACTTTGGCAACAAGAGGCGTCGTACCGGTATattatgcg

F   G   P   G   L   T   I   E   T   V   V   L   R   S   M   A   I   * ttaattatatatctctgcatatatgcaattttgttattttttaataattttcttttactc
1561 ---------+---------+---------+---------+---------+---------+ 1620
     aattaatatatagagacgtatatacgttaaaacaataaaaaattattaaagaaaatgag taaaataagattctaaatggcttatattcttagatgagtgaaaacttagacagagatgtc
1621 ---------+---------+---------+---------+---------+---------+ 1680
     attttattctaagatttaccgaatataagaatctactcacttttgaatctgtctctacag taaagttaattcgttatgcgaaga
1681 ---------+---------+---- 1704
     atttcaattaagcaatacgcttct
```

In the following, some of the media employed in the transformation of the plants, or plant cells, are described:

Am-medium

| | |
|---|---|
| 3.5 g $K_2HPO_4$ | |
| 1.5 g $KH_2PO_4$ | |
| 0.5 g $Na_3$ citrate | |
| 0.1 g $MgSO_4 \times 7H_2O$ | |
| 1 g $(NH_4)_2SO_4$ | |
| 2 g glucose | |
| ad 1 l | |

Medium for sterile shoot culture of tobacco Macroelements ½ of the concentration of MS salts Microelements ½ of the concentration of MS salts Fe-EDTA Murashige and Skoog (MS)

| Myo-inositol | | 100 mg/l |
|---|---|---|
| Sucrose | | 10 mg/l |
| Agar | | 8 g/l |
| Vitamins | Ca panthotenate | 1 mg/l |
| | biotin | 10 mg/l |
| | nicotinic acid | 1 mg/l |
| | pyridoxine | 1 mg/l |
| | thiamine | 1 mg/l |
| pH 5.7 before autoclaving | | |

K3 medium

For the culture of protoplasts of Nicotiana tabacum petit Havana SR1, Nicotiana tabacum Wisconsin 38 and Nicotiana plumaginifolia (Nagy and Maliga, 1976)

| Macroelements | $NH_4NO_3$ | 250 mg/l |
|---|---|---|
| | $KNO_3$ | 2,500 mg/l |
| | $CaCl_2.2H_2O$ | 900 mg/l |
| | $MgSO_4.7H_2O$ | 250 mg/l |
| | $NaH_2PO_4.1H_2O$ | 150 mg/l |
| | $(NH_4)_2SO_4$ | 134 mg/l |
| | $CaHPO_4.1H_2O$ | 50 mg/l |
| Microelements | $H_3BO_3$ | 3 mg/l |
| | $MnSO_4.1H_2O$ | 10 mg/l |
| | $ZnSO_4.4H_2O$ | 2 mg/l |
| | KI | 0.75 mg/l |
| | $Na_2MoO_4.2H_2O$ | 0.25 mg/l |
| | $CuSO_4.5H_2O$ | 0.025 mg/l |
| | $CoCl_2.6H_2O$ | 0.025 mg/l |
| Fe-EDTA | $Na_2EDTA$ | 37.2 mg/l |
| | $FeSO.7H_2O$ | 27.8 mg/l |
| Inositol | | 100 mg/l |
| Sucrose | | 137 g/l (=0.4M) |
| Xylose | | 250 mg/l |
| Vitamins | Nicotinic acid | 1 mg/l |
| | Pyridoxine | 1 mg/l |
| | Thiamine | 10 mg/l |
| Hormones | NAA | 1.0 mg/l |
| | Kinetin | 0.2 mg/l |
| pH 5.6 | | |
| Filter-sterilize | | |

Linsemaier and Skoog medium (Linsemaier and Skoog 1965)

For the culture of regenerating protoplasts and for tissue culture of tobacco tumours and callus. Linsemaier and Skoog (LS) medium is Murashige and Skoog medium (Murashige and Skoog, 1962) with the following modifications:

a higher concentration of thiamine is weighed in 0.4 mg/l instead of 0.1 mg/l;

glycine, pyridoxine and nicotinic acid are missing.

| Macroelements | $NH_4NO_3$ | 1,650 mg/l |
|---|---|---|
| | $KNO_3$ | 1,900 mg/l |
| | $CaCl_2.2H_2O$ | 440 mg/l |
| | $MgSO_4.7H_2O$ | 370 mg/l |
| | $KH_2PO_4$ | 170 mg/l |
| Microelements | $H_3BO_3$ | 6.2 mg/l |
| | $MnSO_4.1H_2O$ | 22.3 mg/l |
| | $ZnSO_4.4H_2O$ | 8.6 mg/l |
| | KI | 0.83 mg/l |
| | $Na_2MoO_4.2H_2O$ | 0.25 mg/l |
| | $CuSO_4.5H_2O$ | 0.025 mg/l |
| | $CoCl_2.6H_2O$ | 0.025 mg/l |
| Fe-EDTA | $Na_2EDTA$ | 37.2 mg/l |
| | $FeSO_4.7H_2O$ | 27.8 mg/l |
| Inositol | | 100 mg/l |
| Sucrose | | 30 g/l |
| Agar | | 8 g/l |
| Vitamins | Thiamine | 0.4 mg/l |
| Hormones: | NAA | 1 mg/l |
| | Kinetin | 0.2 mg/l |
| pH 5.7 before autoclaving | | |

Relating to the transformation of plants, or plant cells, the following literature may be cited:

Aerts M, Jacobs M, Hernalsteens JP, Van Montagu M, Schell J (1983) Induction and in vitro culture of Arabidopsis thaliana crown gall tumours. Plant Sci Lett. 17: 43–50

Atanassov A, Brown DCW (1984) Plant regeneration from suspension culture and mesophyll protoplasts of Medicago sativa L. Plant Cell Tiss Org Cult 3, 149–162

Czernilofsky et al. (1986) Studies of the Structure and Functional Organization of Foreign DNA Integrates into the Genome of Nicotiana tabacum. DNA, Vol. 5, No. 6 (1986), 473

Davey MR, Cocking EC, Freeman J, Pearce N, Tudor I (1980) Transformation of Petunia protoplasts by isolated Agrobacterium plasmid. Plant Sci Lett 18: 307–313

Deblaere R., Bytebier B., De Greve H, Deboeck F, Schell J, van Montagu M, Leemans J (1985) Efficient octopine Ti plasmid-derived vectors for Agrobacterium-mediated gene transfer to plants. Nucleic Acid Research, Vol. 13, No. 13, 4777 (1985)

Fromm ME, Taylor LP, Walbot V (1986) Stable transformation of maize after gene transfer by electroporation. Nature 319: 791–793

Hain, R., Stabel, P., Czernilofsky, A.Pp., Steinbiss, H. H., Herrera-Estrella, L., Schell, J. (1985) Uptake, integration, expression and genetic transmission of a seLectable chimeric gene by plant protoplasts. Molec Gen Genet 199: 161–168

Hernalsteens JP, Thia-Tong L, Schell J, Van Montagu M (1984) An Agrobacterium-transformed Cell culture from the monocot Asparagus officinalis. EMBO J 3:3039–3041

Herrera-Estrella L., De Block M., Messens E., Hernalsteens JP., van Montagu M., Schell J. (1983) EMBO J. 2: 987–995.

Hooykaas-Van Slogteren GMS, Hooykaas PJJ, Schilperoort RA (1984) Expression of Ti-plasmid genes in monocotyledonous plants infected with Agrobacterium tumefaciens Nature 311: 763–764

Horsch RB, Fry JE, Hoffmann NL, EichhoLtz D, Rogers SG, Fraley RT (1985) A simple and general method for transferring genes into plants. Science 277: 1229–1231

Kao KN, Michayluk MR (1980) Plant regeneration from Mesophyll protoplasts of Alfalfa. Z Pflanzenphysiol 96, 135–141

Keller WA, Melchers G (1973) The effect of high pH and calcium on tobacco leaf protoplast fusion. Z Naturforschg 28c: 737–741

Krens FH, Molendijk L, Wullems GJ, Schilperoort RA (1982) in vitro transformation of plant protoplasts with Ti-plasmid DNA. Nature 296: 72–74

Koncz C, Schell J (1986) The promotor of $T_L$-DNA gene 5 controls the tissue-specific expression of chimaeric genes carried by a noval type of Agrobacterium linary vector. Mol. Gen. Genet. (1986) 204: 338–396

Linsemaier DM, Skoog F (1965) Organic growth factor requirements of tobacco tissue cultures. Physiol Plant 18: 100–127

Marton L, Wullems GJ, Molendijk L, Schilperoort PR (1979) In vitro transformation of cultured cells from Nicotiana tabacum by *Agrobacterium tumefaciens*. Nature-277: 1229–131

Nagy JI, Maliga P (1976) Callus induction and plant regeneration from mesophyll protoplasts of Nicotiana sylvestris. Z Pflanzenphysiol 78: 453–455

Otten LABM, Schilperoort RA (1978) A rapid microscale method for the detection of Lysopin and Nopalin dehydrogenase activities. Biochim biophys acta 527: 497–500

Paszkowski J, Shillito RD, Saul M, Mandak V, Hohn T, Hohn B, Potrykus I (1984) Direct gene transfer to plants. EMBO J 3: 2717–2722

Potrykus I, Saul MW, Petruska J, Paszkowski J, Shillito RD (1985) Direct gene transfer to cells of a gramineous monocot. Molec gen genet 199: 183–188

Schenk RU, Hildebrandt AC (1972) Medium and techniques for induction and growth of monocotyledonous and dicotyledonous cell cultures. Can J Bot 50, 199–204

Shillito RD, Paszkowski J. Potrykus I (1983) Agarose plating and Bead type culture technique enable and stimulate development of protoplast-derived colonies in any number of plant species. Pl Cell Rep 2: 244–247

Simons-Schreier A, Studien zur Transformation von Medicago Sativa und zur Expression eines Leghemoglobingens (1bc3) und eines chimaren 1b-cat-Gens wehrend der Symbiore in transgenen Pflanzen [Transformation studies on Medicago Sativa, and studies on the expression of a leghemoglobin gene (1bc3) and a chimeric 1b-cat gene during symbiosis in Transgenic plants]. Ph. D. thesis, Cologne University (1988)

Stuart DA, Strickland SG (1984) Somatic embryogenesis from cell cultures of Medicago sativa L. I. The role of amino acid additions to the regeneration medium. Plant Scit Let 34, 165–174

Stuart DA, Strickland SG (1984) Somatic embryogenesis from cell cultures of Medicago sativa L. II. The interaction of amino acids with ammonium. Plant Sci Let 34, 175–181

Van den Elzen PJM, Townsend J, Lee KY, 8edbrook JR (1985) A chimaeric resistance gene as a selectable marker in plant cells. Plant Mol Biol 5, 299–302

Velten J, Velten L, Hain R, Schell J (1984) Isolation of a dual plant promotor fragment from the Ti Plasmid of *Agrobacterium tumefaciens*. EMSO J 12: 2723–2730

Walker KA, Yu PC, Sato SJ, Jaworski EG (1978) The hormonal control of organ formation in callus of Medicago sativa L. cultured in vitro. Amer J Bot 65(6), 654–659

Walker KA, Sato SJ (1981) Morphogenesis in callus tissue of Medicago sativa: the role of ammonium ion in somatic embryogenesis. Plant Cell Tiss Org Cult 1, 109–121

Wullems GJ, Molendijk L, Ooms G, Schilperoort RA (1981) Differential expression of crown gall tumor markers in transformants obtained after in vitro Agrobacterium tumefaciens—induced transformation of cell wall regenerating protoplasts derived from Nicotiana tabacum. Proc Natl Acad Sci 78: 4344–4348

Zambryski P, Joos H, Genetello C, van Montagu M, Schell J (1983) Ti-plasmid vector for the introduction of DNA into plant cells without altering their normal regeneration capacity, EMBO J 12: 2143–2150

Bernd Reiss, Rolf Sprengel, Hans Will and Heinz Schaller (1984) A new sensitive method for qualitative and quantitative assay of neomycin phosphotransferase in crude cell tracts, GENE 1081: 211–217

Peter H. Schreier, Elisabeth A. Seftor, Jozef Schell and Hans J. Bohnert (1985) The use of nuclear-encoded sequences to direct the light-regulated synthesis and transport of a foreign protein into plant chloroplasts, EMBO J Vol. 4, No. 1: 25–32

Gamborg O. L., Miller R. A. and Ojima K. (1968) Nutrient requirements of suspension cultures of soybean root cells, Experimental Cell Research 50: 151–158

Michael M. Oelck, Phd thesis, 1984, University of Cologne, Federal Republic of Germany, Regeneration von Leguminosen aus Gewebe- und Zellkulturen Furthermore, the following published patent applications may be listed:
EP-A 116 718
EP-A 159 418
EP-A 120 515
EP-A-120 516
EP-A-172 112
EP-A-140 556
EP-A-174 166
EP-A-122 791
EP-A-126 546
EP-A-164 597
EP-A-175 966
WO 84/02913
WO 84/02919
WO 84/02920
WO 83/01176

It will be appreciated that the instant specification and claims are set forth by way of illustration and not limitation, and that various modifications and changes may be made without departing from the spirit and scope of the present invention.

What is claimed is:

1. A process for isolating a resveratrol synthase gene, said process comprising:
   a) isolating total genomic DNA from a plant cell expressing a resveratrol synthase;
   b) cleaving said total genomic DNA into fragments with a restriction endonuclease;
   c) cloning said fragments into vectors;
   d) hybridizing said fragments with a nucleic acid sequence encoding a groundnut resveratrol synthase; and
   e) isolating fragments which specifically hybridize with said nucleic acid sequence encoding a groundnut resveratrol synthase.

* * * * *